United States Patent [19]

Streuff et al.

[11] Patent Number: 5,286,754
[45] Date of Patent: Feb. 15, 1994

[54] PHARMACEUTICAL FORMULATIONS OF CIPROFLOXACIN

[75] Inventors: Bernd Streuff, Wermelskirchen; Helmut Luchtenberg, Niederkassel, both of Fed. Rep. of Germany

[73] Assignee: Bayer Aktiengesellschaft, Leverkusen, Fed. Rep. of Germany

[21] Appl. No.: 246,576

[22] Filed: Sep. 19, 1988

Related U.S. Application Data

[63] Continuation of Ser. No. 3,108, Jan. 14, 1987, abandoned.

[30] Foreign Application Priority Data

Jan. 21, 1986 [DE] Fed. Rep. of Germany ....... 3601566

[51] Int. Cl.$^5$ ............................................... A61K 9/36
[52] U.S. Cl. .................. 514/772.3; 514/781; 424/480; 424/482
[58] Field of Search ................. 424/80, 154, 480, 482; 514/252, 772.3, 781

[56] References Cited

U.S. PATENT DOCUMENTS 4,017,622 4/1977 Minami et al. ...................... 424/250
4,620,007 10/1986 Grohe et al. ........................ 546/156

FOREIGN PATENT DOCUMENTS 0049355 4/1982 European Pat. Off. ... C07D 471/04
0164619 12/1985 European Pat. Off. ..... C07D 63/70
2160519 12/1985 United Kingdom .

OTHER PUBLICATIONS

D. Beermann, et al. "Pharmakokinetik von Ciprofloxacin"—pp. 42–49.
Eur. J. Clin. Microbiol, Apr. 1986. pp. 187–192 "Pharmacokinetics of Ciproflaxacin after Intravenous and Increasing Oral Doses"—Bergan, et al.

*Primary Examiner*—Paul R. Michl
*Assistant Examiner*—Peter F. Kulkosky
*Attorney, Agent, or Firm*—Sprung Horn Kramer & Woods

[57] ABSTRACT

A pharmaceutical formulation comprising by weight 30 to 95% of 1cyclopropyl-6-fluoro-1,4-dihydro-4-oxo-7-(1-piperazinyl)-quinoline-3-carboxylic acid; 4.5 to 25% of a dry binder based on cellulose; 0 to 30% of a disintegration auxiliary based on starch; 0.5 to 10% of a disintegration auxiliary based on a cellulose derivative and/or a cross-linked polyvinyl-pyrrolidone; 0 to 2% of a flow-improving agent, and 0 to 3% of a lubricant. Tablets and capsules made from granules of the formulation, about 0.8 to 2 mm in size, exhibit high bioavailability and excellent storage stability.

1 Claim, No Drawings

PHARMACEUTICAL FORMULATIONS OF CIPROFLOXACIN

This is a continuation of application Ser. No. 003,108, filed Jan. 14, 1987, now abandoned.

The invention relates to pharmaceutical formulations of 1-cyclopropyl-6-fluoro-1,4-dihydro-4-oxo-7-(1-piperazinyl)-quinoline-3-carboxylic acid, also called ciproflaxacin below, processes for their preparation and capsules and tablets containing such formulations.

The use of 1-cyclopropyl-6-fluoro-1,4-dihydro-4-oxo-7-(1-piperazinyl)-quinoline-3-carboxylic acid and its physiologically acceptable derivatives is known from European Patent Application 49,355 and German Patent Application 3,142,854. Lactic acid solutions of ciproflaxacin which are suitable for injection and infusion are described in German Patent Application 3,333,719.

The invention relates to pharmaceutical formulations which can be administered orally and contain 30.0 to 95.0% by weight of 1-cyclopropyl-6-fluoro-1,4-dihydro-4-oxo-7-(1-piperazinyl)-quinoline-3-carboxylic acid; 4.5 to 25.0% by weight of a dry binder based on cellulose; 0.0 to 30.0% by weight of a disintegration auxiliary based on starch; 0.5 to 10.0% by weight of a disintegration auxiliary based on cellulose derivatives and/or cross-linked polyvinylpyrrolidones, 0.0 to 2.0% by weight of a flow-improving agent; and 0.0 to 3.0% by weight of a lubricant.

The pharmaceutical formulations according to the invention combine high biological availability with excellent storage life.

The formulations according to the invention preferably contain 60.0 to 90.0% by weight of 1-cyclopropyl-6-fluoro-1,4-dihydro-4-oxo-7-(1-piperazinyl)-quinoline-3-carboxylic acid as the HCl salt monohydrate.

Pharmaceutical formulations containing 60 to 90% by weight of 1-cyclopropyl-6-fluoro-1,4-dihydro-4-oxo-7-(1-piperazinyl)-quinoline-3-carboxylic acid as the HCl salt monohydrate, 3.0 to 15.0% by weight of a dry binder based on cellulose; 5.0 to 16.0% by weight of a disintegration auxiliary based on starch; 1.0 to 7.0% by weight of a disintegration auxiliary based on cellulose derivatives and/or cross-linked polyvinylpyrrolidone; 0.5 to 1.0% by weight of a flow-improving agent; and 0.5 to 1.0% by weight of a lubricant, and those containing 72.4 to 78.8% by weight of (1-cyclopropyl-6-fluoro-1,4-dihydro-4-oxo-7-(1-piperazinyl)-quinoline-3-carboxylic acid as the HCl salt monohydrate, 7.0 to 9.0% by weight of a dry binder based on cellulose; 9.0 to 12.0% by weight of a disintegration auxiliary based on starch; 4.0 to 5.0% by weight of a disintegration auxiliary based on cellulose derivatives and/or cross-linked polyvinylpyrrolidone; 0.6 to 0.8% by weight of a flow-improving agent; and 0.6 to 0.8% by weight of a lubricant, are furthermore preferred.

However, pharmaceutical formulations which contain 72.4 to 78.8% by weight of 1-cyclopropyl-6-fluoro-1,4-dihydro-4-oxo-7-(1-piperazinyl)-quinoline-3-carboxylic acid as the HCl salt monohydrate, 7.0 to 9.0% by weight of microcrystalline cellulose; 9.0 to 12.0% by weight of corn starch; 4.0 to 5.0% by weight od cross-linked polyvinylpyrrolidone; 0.6 to 0.8% by weight of colloidal silicon dioxide; and 0.6 to 0.8% by weight of magnesium stearate, are especially preferred.

A highly purified microcrystalline cellulose with a molecular weight of 30,000 to 50,000, a particle size of 10 to 50 $\mu$ and a water content of 4 to 6% by weight is preferably used as the dry binder.

Disintegration auxiliaries which can be used are on the one hand the customary types of starch, but in particular corn starch, and on the other hand also cellulose or derivatives and/or cross-linked polyvinylpyrrolidone.

Cellulose derivatives which are customary for this purpose are: for example, sodium carboxymethylcellulose. Cross-linked PVP is commercially available. For example under the tradenames Kollidon ® Cl (BASF AG, Ludwigshafen (D) or Plasdone ® XL (General Aniline & Film Corp., New York (USA)).

Possible flow control agents are pulverulent substances which are frequently also used as powder bases or as powder foundations and which have the properties of imparting a better flowing and pouring capacity to other pulverulent substances with a certain adherence. Suitable substances are, for example, Aerosil ®, a highly pure X-ray-amorphous silicon dioxide (>99.8% SiO$_2$), Aerosil ® 972, a pure silicon dioxide which has hydrophobic properties due to chemically changed methyl groups, and NAL ® and NAL ® RS, a pulverulent product prepared from rice starch (see also H.P. Fiedler, Lexikon der Hilfsstoffe für Pharmazie. Kosmetik und angrenzende Gebiete (Dictionary of Auxiliaries for Pharmacy, Cosmetics and associated fields), Editio Captor KG, Aulendorf i. Württ. (D)).

Lubricants are, for example, talc, calcium stearate, magnesium stearate and solid polyethylene glycols. Magnesium stearate is preferred.

The invention furthermore relates to processes for the preparation of the active compound formulations according to the invention.

For this, the active compound ciprofloxacin is mixed in an amount of 30.0 to 95.0% by weight, based on the total amount of the formulation, with 4.5 to 25.0% by weight of a dry binder based on cellulose, if appropriate with up to 30.0% by weight of a disintegration auxiliary based on starch, with 0.5 to 10.0% by weight of a disintegration auxiliary based on cellulose derivatives and/or cross linked polyvinylpyrrolidones, and if appropriate with up to 2.0% by weight of a flow-improving agent, and if appropriate with up to 3.0% by weight of a lubricant, the mixture is compressed in the dry state, comminuted, sieved and,if appropriate, pressed to tablets or introduced into capsules.

One variant of the process described above comprises granulating the active compound mixture in a fluidized bed granulator by continuously spraying with water or aqueous binder solutions and simultaneously passing in warm air, sieving the resulting granules and if appropriate pressing the mixture to tablets.

In another variant, the active compound ciprofloxacin is granulated with the dry binder based on cellulose, if appropriate in the presence of a disintegration auxiliary based on starch and with the other disintegration auxiliary based on cellulose derivatives and/or cross-linked polyvinylpyrrolidone and the granules are sieved and, if appropriate, mixed with the remaining additives and the mixture is pressed into tablets or introduced into capsules.

Granules with a cross-section of 0.8 to 2 mm for further processing to tablets or capsules are advantageously provided by the sieving-out process.

A procedure can also preferably be followed in which the active compounds are mixed with corn starch, Avicel ® and Aerosil ®, these mixtures are combined, after granulation, with cross-linked polyvinylpyrrolidone and magnesium stearate and the resulting material is then pressed to tablets.

The formulations according to the invention exhibit a broad antibacterial spectrum against Gram-positive and Gram-negative germs, in particular against Enterobacteriaceae, above all also against those which are resistant towards various antibiotics, such as, for example, penicillins, cephalosporins, aminoglycosides, sulphonamides and tetracyclines, coupled with a low toxicity.

These useful properties enable them to be used as chemotherapeutic active compounds in medicine.

The formulations according to the invention are active against a very broad spectrum of micro-organisms. With their aid, it is possible for Gram-negative and Gram-positive bacteria and bacteria-like micro-organisms to be combated and for the diseases caused by these pathogens to be prevented, alleviated and/or cured.

The formulations according to the invention are particularly active against bacteria and bacteria-like micro-organisms. They are therefore particularly suitable in human and veterinary medicine for the prophylaxis and chemotherapy of local and systemic infections caused by these pathogens.

Local and/or systemic diseases which are caused by the following pathogens or by mixtures of the following pathogens, for example, can be treated and/or prevented: Micrococcaceae, such as Staphylococci, for example Staph. aureus and Staph. Epidermidis, (Staph. = Staphyloccoccus); Lactobacteriaceae, such as Streptococci, for example Streptococcus pyogenes, α- and β-haemolysing Streptococci and non-γ-haemolysing Streptococci, Enterococci and Diplocuccus pneumoniae (pneumococci) Enterobacteriaceae, such as Escherichiae bacteria of the Escheridrion group, for example *Escherichia coli*, Enterobacter bacteria, for example *E. aerogenes* and *E. Cloacae* (E.=Enterobacter), Klebsiella bacteria, for example K. pneumoniae (K.=Klebsiella), Serratia, for example *Serratia marcescens*, Proteae bacteria of the Proteus group; Proteus, for example *Pr. vulgaris, Pr. morganii, Pr. retgeri* and *Pr. mirabilis* (Pr.=Proteus); Pseudomonadaceae, such as Pseudomonas bacteria, for example *Ps. aeruginosa* (Ps.=Pseudomonas); Bacteroidaceae, such as Bacteriodes bacteria, for example *Bacteroides fragilis*; Mycoplasma, for example Mycoplasma pneumonia, and also mycobacteria, for example *Mycobacterium tuerculosis, Mycobacterium leprae* and atypical microbacteria.

The above list of pathogens is merely by way of example and is in no way to be interpreted as limiting. Examples which may be mentioned of diseases which can be prevented, alleviated and/or cured by the formulations according to the invention are: otitis; pharyngitis; pneumonia; peritonitis; pyelonephritis; cystitis; endocarditis; systemic infections; bronchitis; arthritis; local infections; and septic diseases.

The present invention also includes pharmaceutical formulations in dosage units. This means that the formulations are in the form of individual parts, for example tablets, dragees, capsules and pills, the active compound content of which correspond to a fraction or a multiple of an individual dose. The dosage units can contain, for example, 1, 2, 3 or 4 individual doses or ½, ⅓ or ¼ of an individual dose. An individual dose preferably contains the amount of active compound which is given in one administration and which usually corresponds to a whole, one half, one third or one quarter of a daily dose.

The tablets, dragees, capsules, pills and granules can be provided with the customary coatings and shells, optionally containing opacifying agents, and can also be of such composition that they release the active compound or compounds only or preferentially in a certain part of the intestinal tract, optionally in a delayed manner, examples of embedding compositions which can be used being polymeric substances and waxes.

The active compound or compounds can also be in a micro-encapsulated form, if appropriate with one or more of the abovementioned excipients.

The formulation forms according to the invention can also contain coloring agents, preservatives and additives for improving the smell and taste, for example peppermint oil and eucalyptus oil, and sweeteners, for example saccharin.

The following examples relate to the HCl salt monohydrate, other salts, derivatives or the pure base can likewise be used.

EXAMPLES

| | | |
|---|---|---|
| 1. | Ciprofloxacin monohydrate | 583.0 mg |
| | ( 500 mg of betain) | |
| | microcristalline cellulose | 55.0 mg |
| | moist corn starch | 72.0 mg |
| | Crosslinked PVP | 30.0 mg |
| | Siliciumdioxide | 5.0 mg |
| | magnesium stearate | 5.0 mg |
| | non-laquered tablet | 750.0 mg |
| | lacquer shell: | |
| | Hydroxypropylmethylcellulose 15 cp | 6.2 mg |
| | PEG 4000 | 200.0 mg |
| | titanium dioxide | 2.0 mg |
| | lacquered tablet | 760.0 mg |
| 2. | Ciprofloxacin monohydrate | 291.5 mg |
| | ( 250 mg of betain) | |
| | microcristalline cellulose | 27.5 mg |
| | moist corn starch | 36.0 mg |
| | Crosslinked PVP | 15.0 mg |
| | Siliciumdioxide | 2.5 mg |
| | magnesium stearate | 2.5 mg |
| | non-laquered tablet | 375.0 mg |
| | lacquer shell: | |
| | Hydroxypropylmethylcellulose 15 cp | 3.9 mg |
| | PEG 4000 | 1.3 mg |
| | titanium dioxide | 1.3 mg |
| | lacquered tablet | 381.5 mg |
| 3. | Ciprofloxacin monohydrate | 233.2 mg |
| | ( 200 mg of betain) | |
| | microcristalline cellulose | 22.0 mg |
| | moist corn starch | 28.8 mg |
| | Crosslinked PVP | 12.0 mg |
| | Silicium dioxide | 2.0 mg |
| | magnesium stearate | 2.0 mg |
| | non-lacquered tablet | 300.0 mg |
| | lacquer shell: | |
| | Hydroxypropylmethylcellulose 15 cp | 3.0 mg |
| | PEG 4000 | 1.0 mg |
| | titanium dioxide | 1.0 mg |
| | lacquered tablet | 305.0 mg |
| 4. | Ciprofloxacin monohydrate | 116.6 mg |
| | ( 100 mg of betain) | |
| | microcristalline cellulose | 11.0 mg |
| | moist corn starch | 14.4 mg |
| | Crosslinked PVP | 6.0 mg |
| | Siliciumdioxide | 1.0 mg |
| | magnesium stearate | 1.0 mg |
| | non-lacquered tablet | 150.0 mg |
| | lacquer shell: | |
| | Hydroxypropylmethylcellulose 15 cp | 1.8 mg |
| | PEG 4000 | 0.6 mg |
| | titanium dioxide | 0.6 mg |
| | lacquered tablet | 153.0 mg |
| 5. | Ciprofloxacin monohydrate | 874.5 mg |
| | ( 750 mg of betain) | |
| | microcristalline cellulose | 82.5 mg |
| | moist corn starch | 108.0 mg |

|   |   |   |
|---|---|---|
|   | Crosslinked PVP | 45.0 mg |
|   | Siliciumdioxide | 7.5 mg |
|   | magnesium stearate | 7.5 mg |
|   | non-lacquered tablet | 1,125.0 mg |
|   | lacquer shell: | |
|   | Hydroxypropylmethylcellulose 15 cp | 9.0 mg |
|   | PEG 4000 | 3.0 mg |
|   | titanium dioxide | 3.0 mg |
|   | lacquered tablet | 1,140.0 mg |
| 6. | Ciprofloxacin monohydrate | 58.3 mg |
|   | ( 50 mg of betain) | |
|   | microcristalline cellulose | 40.5 mg |
|   | moist corn starch | 7.2 mg |
|   | Crosslinked PVP | 3.0 mg |
|   | Siliciumdioxide | 0.5 mg |
|   | magnesium stearate | 0.5 mg |
|   | Contents of capsule | 110.0 mg |
|   | Weight of empty capsule | 35.0 mg |
|   | Filled capsule | 145.0 mg |

It will be understood that the specification and examples are illustrative but not limitative of the present invention and that other embodiments within the spirit and scope of the invention will suggest themselves to those skilled in the art

What is claimed:

1. A pharmaceutical formulation of high biological availability and storage life consisting of by weight 583 parts of 1-cyclopropyl-6-fluoro-1,4-dihydro-4-oxo-7-(1-piperazinyl)-quinoline-3-carboxylic acid HCl monohydrate; 55 parts of microcrystalline cellulose; 72 parts of moist starch; 30 parts of cross-linked polyvinyl-pyrrolidone; 5 parts of silicon dioxide; and 5 parts of magnesium stearate.

* * * * *